United States Patent [19]
Soled et al.

[11] Patent Number: 5,391,532
[45] Date of Patent: Feb. 21, 1995

[54] ZIRCONIUM HYDROXIDE SUPPORTED METAL AND HETEROPOLYACID CATALYSTS

[75] Inventors: Stuart L. Soled, Pittstown; Gary B. McVicker, Califon; Sabato Miseo, Pittstown; William E. Gates, Lebanon Township, Hunterdon County, all of N.J.

[73] Assignee: Exxon Research and Engineering Company, Florham Park, N.J.

[21] Appl. No.: 58,602

[22] Filed: May 6, 1993

[51] Int. Cl.$^6$ .................. B01J 27/188; B01J 27/185; B01J 21/08

[52] U.S. Cl. .................. 502/210; 50/242; 50/258; 50/259; 50/260; 50/261; 50/262; 50/213; 50/349

[58] Field of Search ........... 502/210, 242, 258, 259, 502/260, 261, 262, 213, 349

[56] References Cited

U.S. PATENT DOCUMENTS

| | | |
|---|---|---|
| 3,346,657 | 10/1967 | Henke et al. . |
| 3,660,506 | 5/1972 | Banks et al. . |
| 3,865,751 | 2/1975 | Banks et al. . |
| 4,071,471 | 1/1978 | Banks et al. . |
| 4,473,705 | 9/1984 | Miyamori et al. .................. 502/210 |
| 4,912,264 | 3/1990 | Takeshita et al. . |
| 4,918,041 | 4/1990 | Hollstein et al. . |
| 4,956,519 | 9/1990 | Hollstein et al. . |
| 5,037,838 | 8/1991 | Zimmerman et al. .............. 502/210 |
| 5,164,354 | 11/1992 | Aldridge et al. .................... 502/210 |

FOREIGN PATENT DOCUMENTS 59005130 6/1982 Japan .
04005254 4/1990 Japan .

OTHER PUBLICATIONS

J. Chem. Soc. Faraday Trans., 1991, 87(5) 749–753 "Catalytic Activity Supported Heteropoly Acids for Reaction requiring Strong Acid Centers".
Catalysis Letters 12(1992) 63–72, "Heterogenous Catalysis by Heteropoly Compounds. An attempt of molecular design of practical solid acid catalysts".
Stud. Surf. Sci. & Catal. 44 (1989) 267–78 "Catalysis By Heteropoly Compounds".

*Primary Examiner*—Asok Pal
*Assistant Examiner*—E. O. Irinski
*Attorney, Agent, or Firm*—Estelle C. Bakun

[57] ABSTRACT

The present invention is directed to novel catalyst compositions, their preparation, and their use in a selective paraffin isomerization process. The solid acid catalyst compositions comprise a zirconium hydroxide support, a Group VIII metal, and a heteropolyacid selected from the group consisting of the exchanged aluminum salt of 12-tungstophosphoric acid, the exchanged salt of 12-tungstosilicic acid, and mixtures thereof. The use of said catalysts in an isomerization process comprises contacting said catalysts with a feed comprising $C_n$ or $C_{n+}$ paraffins, wherein $n=4$.

7 Claims, 5 Drawing Sheets

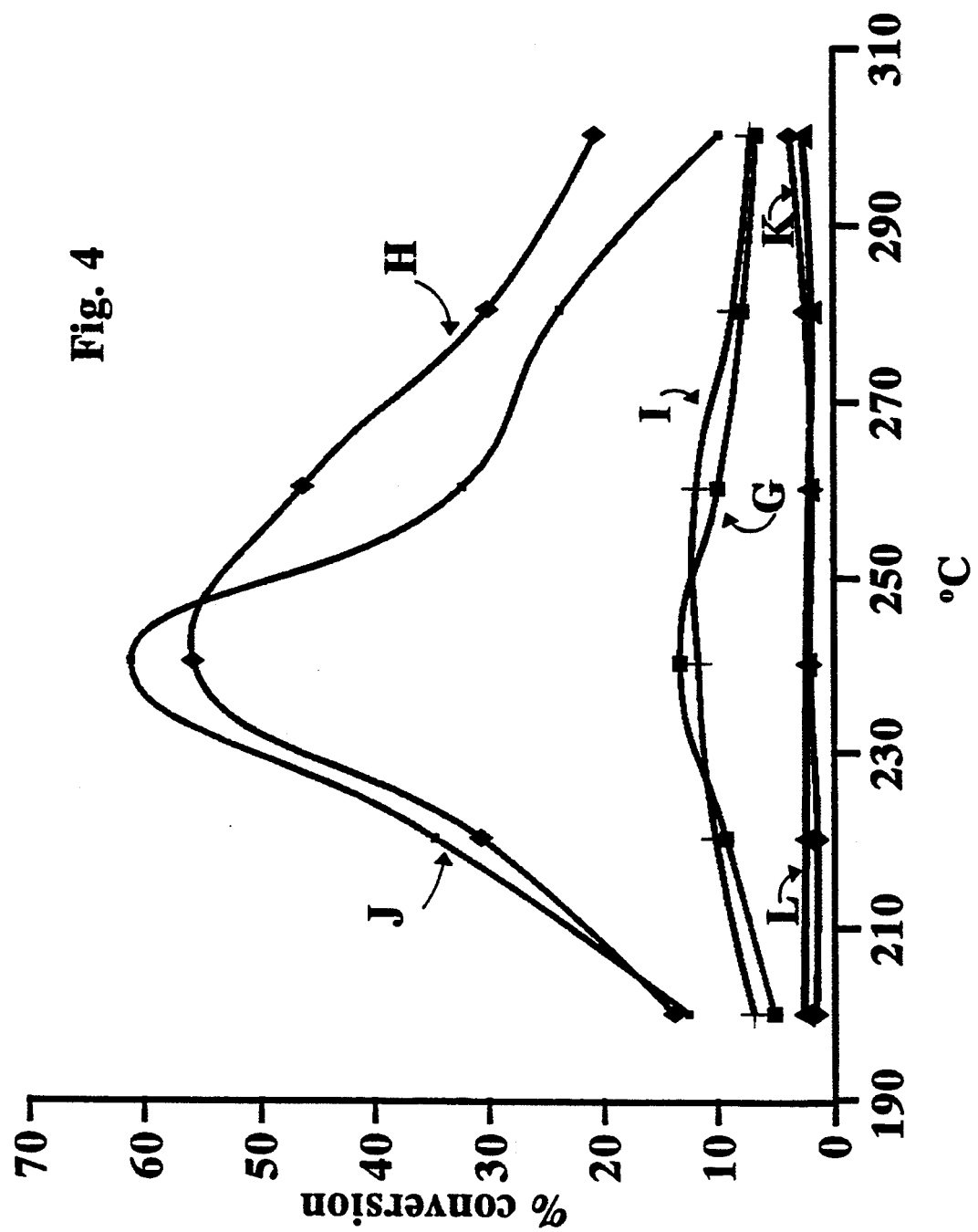

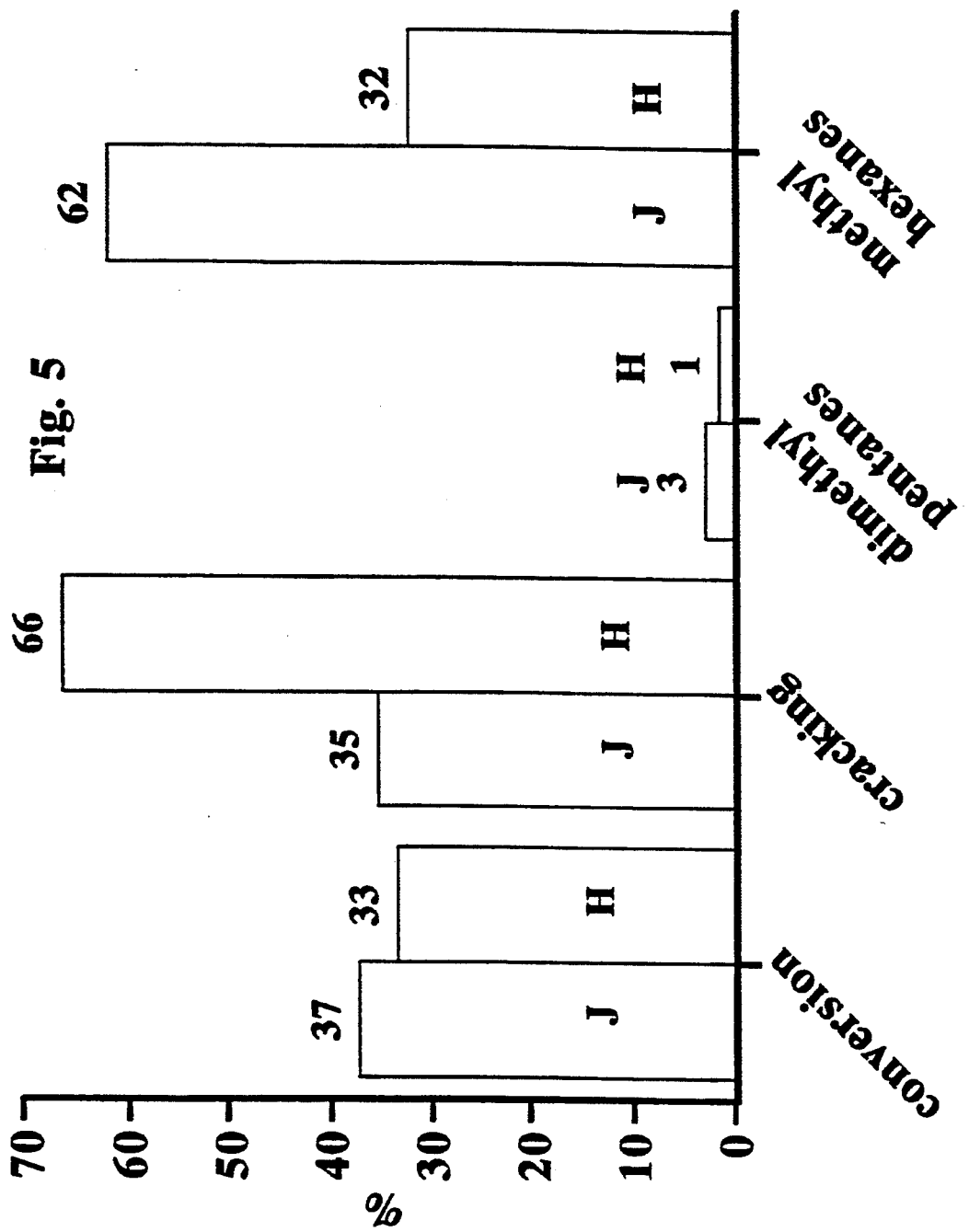

ZIRCONIUM HYDROXIDE SUPPORTED METAL AND HETEROPOLYACID CATALYSTS

BACKGROUND OF THE INVENTION

The increasing emphasis on obtaining high octane non-aromatic fuel molecules has increased the search for environmentally compatible solid acid catalysts, primarily oxides, for use in such processes as paraffin isomerization and alkylation. In the area of paraffin isomerization, the solid acid catalyst should provide good activity at low temperature since thermodynamic equilibrium generally favors multibranched isomers, with high octane value, at lower temperature. In addition to maximizing product branching it is important to limit the amount of competing reactions, predominantly cracking, during isomerization. These cracking reactions are particularly problematic for acyclic paraffin feed molecules $C_7+$ or larger.

The most commonly used catalysts in n-paraffin ($C_5$ and $C_6$) isomerization include Pt supported on zeolites such as mordenite, or on highly chlorided aluminas which in the presence of continuous chlorine addition to the feed exist as aluminum trichloride supported on alumina. What is needed in the art is an oxide based catalyst that can isomerize n-paraffins at low temperatures and in particular form very little cracked products with $C_7+$ feeds. Furthermore, such catalysts would alleviate the environmental concerns associated with the inconvenient, environmentally detrimental chlorine addition required during operating aluminum chloride based isomerization catalysts.

SUMMARY OF THE INVENTION

The supported heteropolyacid catalysts of the present invention catalyze the isomerization of n-paraffins, such as heptane, at temperatures comparable to those found using Pt-containing acidic zeolites such as mordenite or using strong acids based on or related to sulfated zirconia ($ZrO_2/SO_4$). Unexpectedly, the amount of cracking of $C_7+$ paraffins is substantially reduced.

The present invention is directed to novel catalyst compositions, their preparation, and their use in a selective paraffin isomerization process. The present invention is directed to novel solid acid catalyst compositions comprising a zirconium hydroxide support, a Group VIII metal, and a heteropolyacid selected from the group consisting of the exchanged aluminum salt of 12-tungstophosphoric acid, the exchanged salt of 12-tungstosilicic acid, and mixtures thereof. The use of said catalysts in an isomerization process comprises contacting said catalysts with a feed comprising $C_n$ or $C_n+$ paraffins, wherein n=4.

The process of making such catalysts comprises the steps of:

(a) impregnating a heteropolyacid selected from the group consisting of the exchanged aluminum salt of 12-tungstophosphoric acid, the exchanged aluminum salt of 12-tungstosilicic acid, and mixtures thereof onto a zirconium hydroxide support;

(b) impregnating Group VIII metal onto said support before, during or subsequent to step (a);

(c) activating said impregnated zirconium hydroxide support prior to and following said impregnation step (b) if said Group VIII metal is impregnated subsequent to step (a) or activating said impregnated support after said impregnation of a heteropolyacid if said Group VIII metal is impregnated before or during step (a) to form a catalyst.

BRIEF DESCRIPTION OF THE DRAWINGS

FIG. 4 shows the % conversion of n-heptane vs. temperature in ° C. for catalysts G, H, I, J, K and L which are analogous to catalysts A, B, C, D, E, and F except that the support is silica instead of zirconium hydroxide and no aluminum is added to catalysts K and L. The 12-tungstophosphoric acid and platinum incorporated via chloroplatinic acid (J) and the exchanged aluminum 12-tungstophosphoric acid and platinum incorporated via chloroplatinic acid (H) show low temperature activity. The aluminum did not affect catalyst activity of 12-tungstophosphoric acid and the tungsten oxide (ammonium metatungstate precursor) based catalysts are inactive as is catalyst G having platinum incorporated via platinum tetrammine hydroxide.

FIG. 5 shows the conversion of n-heptane, % selectivity to cracked products ($C_6-$), dimethyl pentanes, and methyl hexanes for catalysts H and J.

Catalyst Designation of Figures

Figure 1:
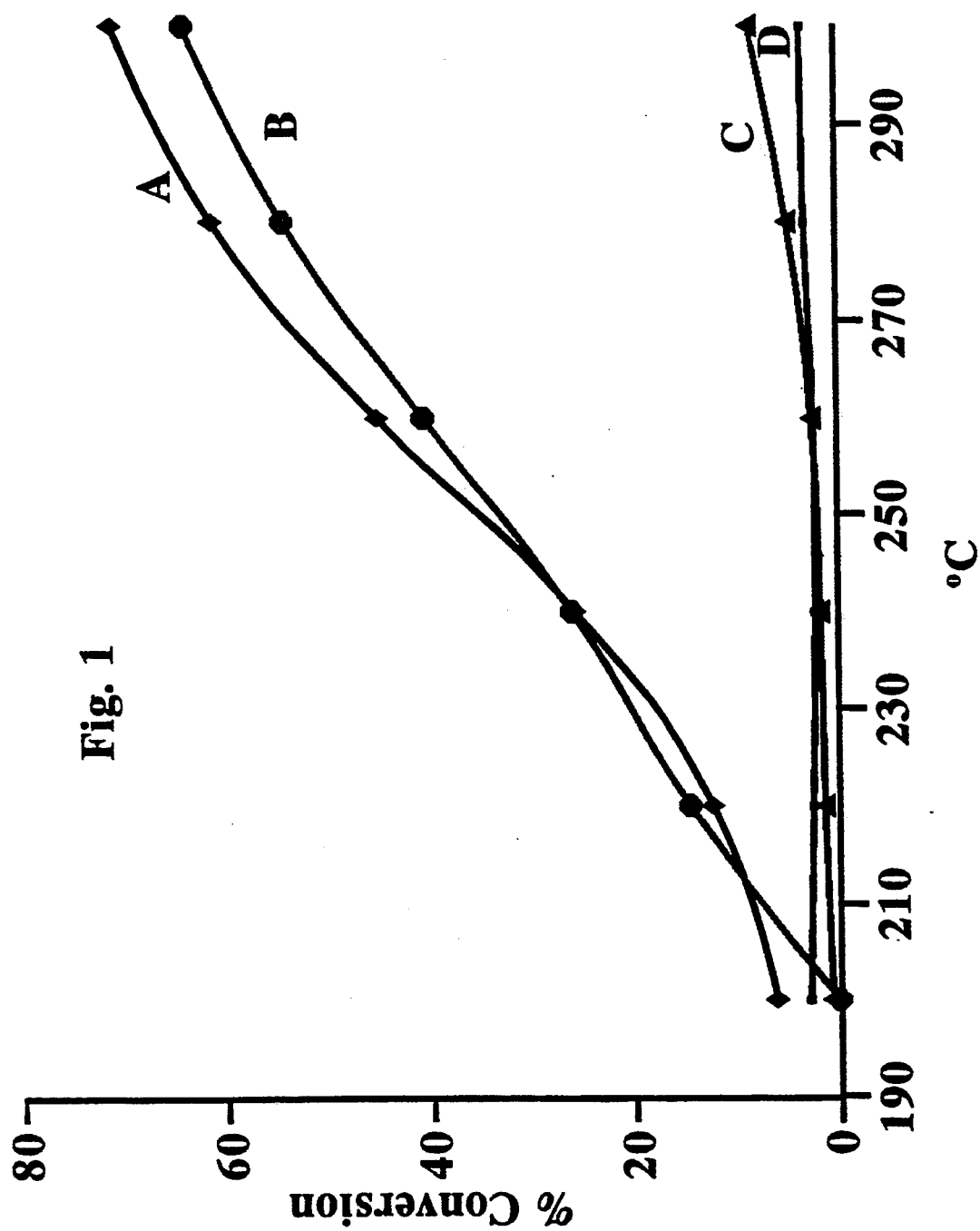
FIG. 1 shows the % conversion of n-heptane vs. temperature for four catalysts supported on zirconium hydroxide. Catalysts A and B are exchanged aluminum 12-tungstophosphoric acid and platinum with the platinum precursor being either tetrammine platinum hydroxide or chloroplatinic acid, respectively. Catalysts C and D are 12-tungstophosphoric acid and platinum with the platinum precursor being either tetrammine platinum hydroxide or chloroplatinic acid, respectively. The figure shows that on a $Zr(OH)_4$ support, the exchanged aluminum salt of 12-tungstophosphoric acid (i.e., $Al_{.83}H_{.5}PW_{12}O_{40}$) is more active than the 12-tungstophosphoric acid ($H_3PW_{12}O_{40} \cdot 6H_2O$). The aluminum 12-tungstophosphoric acid and platinum catalysts show low temperature (210°–270° C.) activity for $C_7$ isomerization, whereas the 12-tungstophosphoric acid and platinum catalysts do not.

A: $Pt/Al_{.83}H_{.5}PW_{12}O_{40}/Zr(OH)_4$*
B: $Pt/Al_{.83}H_{.5}PW_{12}O_{40}/Zr(OH)_4$**
C: $Pt/H_3PW_{12}O_{40}/Zr(OH)_4$*
D: $Pt/H_3PW_{12}O_{40}/Zr(OH)_4$**
E: $Pt/WO_3(\&Al)/Zr(OH)_4$*
F: $Pt/WO_3(\&Al)/Zr(OH)_4$**
G: $Pt/Al_{.83}H_{.5}PW_{12}O_{40}/SiO_2$*
H: $Pt/Al_{.83}H_{.5}PW_{12}O_{40}/SiO_2$**
I: $Pt/H_3PW_{12}O_{40}/SiO_2$*
J: $Pt/H_3PW_{12}O_{40}/SiO_2$**
K: $Pt/WO_3/SiO_2$*
L: $Pt/WO_3/SiO_2$**

\* 0.3 wt. % platinum incorporated using tetrammine platinum hydroxide

\*\* 0.3 wt. % platinum incorporated using chloroplatinic acid

DETAILED DESCRIPTION OF THE INVENTION

Heteropoly acids form by condensation of two or more oxyacids, e.g., phosphoric or silicic acid with tungstic acid, and contain large polyoxometallate anions with interstitial hydrated protons and variable levels of water of hydration. The heteropolyacids are soluble in water or polar oxygenated hydrocarbons, such as alcohols or ethers. The particular heteropoly acids of the present catalysts are acids with anions adopting the well known Keggin structure and are represented by formulas: $H_3PW_{12}O_{40} \cdot 6H_2O$ (phosphotungstic acid or 12-tungstophosphoric acid), and $H_4SiW_{12}O_{40} \cdot 6H_2O$ (12-tungstosilicic acid or silicotungstic acid). They contain a central tetrahedral $PO_4$ or $SiO_4$ group connected to 12 surrounding $WO_3$ octahedra and can be considered the condensation product of phosphoric or silicic acid with tungstic acid.

These water soluble acids can be deposited on supports by impregnation techniques well known to those skilled in the art such as by an incipient wetness technique.

The supports of the instant invention, silica when the heteropoly acid is 12-tungstophosphoric acid, 12-tungstosilicic acid, the exchanged aluminum salt of 12-tungstophosphoric acid, and the exchanged aluminum salt of 12-tungstosilicic acid, and zirconium hydroxide when the heteropoly acid is the exchanged aluminum salts of 12-tungstophosphoric acid and 12-tungstosilicic acid are commercially available or may be prepared by well known techniques. For example, the zirconium hydroxide may be precipitated, at a pH of 9, from a solution of zirconyl chloride and ammonium hydroxide followed by washing to remove residual chloride ions. Preferably the supports will be thermally treated prior to use. Preferably the silica will be calcined at about 500° C. and the zirconium hydroxide at about 110° C. Partially exchanged as used herein means that $Al^{+3}$ is substituted into the heteropolyacid to replace some, but not all, of the protons. The amount of exchange depends upon the amount of aluminum utilized and is readily determinable by one skilled in the art. Preferably between 0.5 and 2.75 of the protons are exchanged with $Al^{+3}$ cations, more preferably between 2.25 and 2.5 will be exchanged. It is obvious to one skilled in the art that all of the protons cannot be exchanged or acidity will be lost. For example

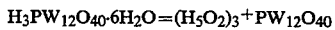

is exchanged to

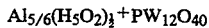

in which 2.5 of the 3 hydrated protons have been replaced.

The heteropoly acid (HPA) and Group VIII metal may be coimpregnated onto the support, the Group VIII metal impregnated first, or the Group VIII metal can be impregnated supsequent to the HPA. Preferably, however, the HPA is impregnated first followed by impregnation of the Group VIII metal.

The Group VIII metal can be impregnated onto the support by any of the techniques known to those skilled in the art. For example, the incipient wetness technique, or an absorption technique from a dilute or concentrated solution, with subsequent filtration or evaporation to effect uptake of the metallic Group VIII component. The impregnation can be carried out under a variety of conditions known to those skilled in the art, including ambient and elevated temperatures, and atmospheric and superatmospheric conditions.

The amount of Group VIII metal will range from about 0.01 to about 10 wt. %, preferably about 0.2 to about 1.0 wt. %, and most preferably about 0.3 to about 0.7 wt. %.

The amount of heteropolyacid to be impregnated onto the support will range from about 0.01 to about 60 wt. %, preferably about 10 to about 50 wt. %, and most preferably about 25 to about 40 wt. %.

Once the heteropolyacid is impregnated onto the support, the support is dried at about 100° to about 120° C. for at least 4 hours followed by calcination at about 250° to about 500° C., preferably 300° C. for at least 4 hours. This drying and calcination is herein referred to as activation. If coimpregnation is used, only one drying and calcination under the above conditions will be carried out. If the Group VIII metal is impregnated prior to the HPA, only the drying step will be carried out and activation will be conducted following the HPA impregnation. If the HPA is impregnated first followed by the Group VIII metal, activation will occur before and after the impregnation of the Group VIII metal. If the HPA and Group VIII metal are coimpregnated, activation will occur following coimpregnation.

The Group VIII metals useable for the present invention catalysts are any of the Group VIII metals of the periodic table, namely iron, cobalt, nickel, ruthenium, rhodium, palladium, osmium, iridium, platinum and mixtures thereof. Preferably a Group VIII noble metal will be employed, most preferably platinum.

Applicants have found that the platinum metal precursor has little effect on catalyst activity for 12-tungstophosphoric acid or the exchanged aluminum salt of 12-tungstophosphoric acid when the support is zirconium hydroxide. However, the platinum metal precursor becomes an important parameter with respect to catalyst selectivity. Applicants have found that with a zirconium hydroxide support the exchanged aluminum 12-tungstophosphoric acid with platinum incorporated by use of a tetrammine platinum hydroxide precursor, dramatically reduces the selectivity to cracked products compared to one prepared with chloroplatinic acid as the precursor. Additionally, applicants have found that although the addition of aluminum to 12-tungstophosphoric acid on silica is not critical, the platinum precursor is. Only those catalysts made with chloroplatinic acid are active; platinum tetrammine hydroxide produces inferior catalysts. The examples will make this readily evident. Hence, when preparing a catalyst comprising the aluminum salt of 12-tungstophosphoric acid and Group VIII metal on a zirconium hydroxide support, it is preferable that the Group VIII metal precursor be present in a cationic form; the resulting isomerization reaction is accompanied by less cracking side reactions. However, the Group VIII precursor can also be added as an anionic complex in which case activity will be comparable but the increased selectivity will not be afforded. When preparing a catalyst comprising 12-tungstophosphoric acid and Group VIII metal on silica, the Group VIII metal precursor must be present as an anionic complex. Any Group VIII metal precursors meeting this criteria are acceptable for use.

Cationic form means the Group VIII metal is present as a cation, e.g., tetrammine platinum hydroxide, tetrammine platinum chloride, and dinitrodiammineplatinum (II), or any other cationic forms of Group VIII compounds known to those skilled in the art can be used. Anionic complexes means the Group VIII metal is contained in an anionic complex such as e.g. $(PtCl_4)^{-2}$ wherein the complex is negatively charged. Examples of suitable anionic complexes are chloroplatinic acid (known as hydrogen hexachloroplatinate (IV)), ammonium tetrachloroplatinate (II), ammonium hexachloroplatinate (IV), bromoplatinic acid (known as hydrogen hexabromoplatinate (IV)), and chloroiridic acid. The above lists of compounds containing Group VIII metals as cations or in anionic complexes are merely illustrative and not meant to be limiting.

The catalysts of the present invention are useful in an isomerization reaction. The isomerization reaction is carried out at temperatures at or below about 500° C., preferably 25°–250° C.; 15 to 3000 psi $H_2$, preferably 100 to 1500 psi $H_2$; 1 to 100, preferably 2 to 12.0 WHSV; and $H_2$/paraffin ratio of 1:1 to 10:1, preferably 3:1 to 7:1.

The exchanged aluminum salt of 12-tungstophosphoric acid and platinum on zirconium hydroxide exhibits low temperature activity for $C_7$ isomerization. It exhibits increasing activity from about 220° C. to about 300° C. and the selectivity to cracked products at 30% conversion is only 10%.

The 12-tungstophosphoric acid or the exchanged aluminum salt and platinum supported on silica also exhibits low temperature activity between about 210° C. and 260° C. Hence, the catalysts of the present invention are particularly useful for low temperature isomerization processes at temperatures where conventional (e.g. supported tungsten oxide) catalysts are inadequate.

The following examples are illustrative of the invention and are not meant to be limiting.

EXAMPLES

A suite of catalysts was prepared that contained the equivalent of 40 wt. % $WO_3$ using 12-tungstophosphoric acid, the exchanged aluminum salt of 12-tungstophosphoric acid ($Al_{.83}H_{.5}PW_{12}O_{40}$ salt), ammonium metatungstate, and ammonium metatungstate with added aluminum cations. These precursors were impregnated onto $\gamma$-$Al_2O_3$, $SiO_2$, amorphous $SiO_2$-$Al_2O_3$ and $Zr(OH)_4$. 0.3 wt. % Pt is added to these supported heteropoly acids by using both chloroplatinic acid (Pt present as an anionic complex) or as tetrammine platinum hydroxide (Pt present in a cationic form). In all cases the supported heteropoly acid or ammonium metatungstate was calcined at 300° C. and the platinum precursor was then decomposed at 300° C.

Example 1

Preparation of 12-Tungstophosphoric Acid

Dissolve 100 grams of sodium tungstate and 16 grams disodium phosphate in 1500 cc of water and heat to 80° to 90° C. for 30 minutes. To this add 80 cc of concentrated HCl dropwise. A precipitate forms after about half of the HCl is added. After 30 minutes of stirring, add 60 cc ether, stir and shake. Three layers form. The lower layer is washed three times with water and enough ether is added to form three additional layers. This is repeated several times and finally the lower layer is dried by aspiration with air. Alternatively a commercial source of 12-tungstophosphoric acid can be used, and it is first dried for 2 to 5 hours at 110° C. In both cases, the product shows the characteristic cubic x-ray diffraction pattern spectrum characteristic of the Keggin structure. See, e.g., G. M. Brown, M. R. Spirlet, W. R. Busing and H. A. Levy, Acta Cryst. B33, 1038–46 (1977).

Example 2

Preparation of 40% Phosphotungstic Acid (HPW) on Supports

Four different supports were used. A commercial supply of reforming grade gamma alumina with a surface area of 180 m²/g, a commercial supply of $SiO_2$(350 m²/g), a commercial supply of an amorphous $SiO_2$-$Al_2O_3$(350 m²/g), and a laboratory prepared sample of $Zr(OH)_4$. The first three commercially prepared supports were calcined at 500° C. prior to use. The $Zr(OH)_4$ was prepared by precipitating an aqueous solution of zirconyl chloride with ammonium hydroxide to reach a pH of 9 and washing the precipitate repeatedly with a pH 9 ammonium hydroxide solution to remove residual chloride ions. This was then dried at 100° C. and used as support with (220 m²/g) surface area. In each case 31.8 gm of the 12-tungstophosphoric acid hexa-hydrate was dissolved in enough water to impregnate by incipient wetness 45 grams of the above four supports. These were then dried at 110° C. overnight and then calcined at 300° C. in air for three hours.

Example 3

Preparation of 40% Aluminum-Phosphotungstic Acid (Al-HPW) ($Al_{.83}H_{.5}PW_{12}O_{40}$) on Supports The same four supports were used as in Example 2. 35.3 grams of 12-tungstophosphoric acid and 3.59 g of aluminum nitrate nonahydrate were dissolved in sufficient water to impregnate by incipient wetness 50 grams of each support. These were then dried at 110° C. overnight and then calcined at 300° C. in air for three hours.

Example 4

Preparation of 40% $WO_3$ on Supports

The same four supports were used as in Examples 1 and 2. 21.6 grams of a commercially available ammonium metatungstate (92.3% $WO_3$) were dissolved in sufficient water to impregnate by incipient wetness 30 grams of each support. These were then dried at 110° C. overnight and then calcined at 300° C. in air for three hours.

Example 5

Preparation of 40% $WO_3$ (with Al) on Supports

The same four supports were used as in Examples 1, 2, and 3. 21.6 grams of a commercially available ammonium metatungstate (92.3% $WO_3$) and 2.16 grams of aluminum nitrate nonahydrate were dissolved in sufficient water to impregnate by incipient wetness 30 grams of each support. The Al:W molar ratio was the same as for the heteropolyacids of Example 2. These were then dried at 110° C. overnight and calcined at 300° C. in air for three hours.

Example 6

Properties and Initial Acidity Characterization of Supported Heteropoly Acids and $WO_3$ Catalysts Table 1 lists the acid strength parameters for the catalysts prepared in Examples 2–5 when run in the 2-methyl-2 pentene reaction test (2MP2), (reference test: Kramer and McVicker, Accounts of Chemical Research, 19, 78 (1986)).

The formation rates and rate ratios of the product hexene isomers of this test reaction reflect the acid site concentration and strength of the catalyst respectively. The product hexene isomers formed include 4-methyl-pent-2-ene (4MP2), t-3-methylpent-2-ene (t-3MP2), and 2,3 dimethylbute-2-ene (2,3 DMB2). 4MP2 requires only a double bond shift, a reaction occurring on weak acid sites. 3MP2 requires a methyl group shift (i.e., stronger acidity than double bond shift), whereas 2,3DMB2 requires even stronger acidity to produce a second methyl branch. For a homologous series of solid acids, differences in t-3MP2 rates normalized with respect to surface area reflect the density of acid sites possessing strengths sufficient to catalyze the skeletal isomerization. Since skeletal isomerization rates generally increase with increasing acid strength, the ratio of methyl group migration rate to double bond shift rate should increase with increasing acid strength. The use of rate ratios, in lieu of individual conversion rates is preferable since differences in acid site populations are normalized.

TABLE 1

SUMMARY OF SUPPORTED HETEROPOLY ACIDS
Precursor Effects

| Rate Ratios at 250° C. 1 Hr. On Stream | Support only | 40% 12-Tungstophosphoric Acid (300° C.)* | 40% Aluminum Exchanged 12-Tungstophosphoric Acid $Al_{.83}H_{.5}PW_{12}O_{40}$ (300° C.)* | 40% $WO_3$ Ammonium Metatungstate (300° C.)* |
|---|---|---|---|---|
| 3MP2/4MP2; 2,3DMB2/4MP2 | $Zr(OH)_4$ n.a. | $Zr(OH)_4$ 0.79; 0.066 | $Zr(OH)_4$ 2.12; 0.37 | $Zr(OH)_4$ 1.11; 0.094 |
| 3MP2/4MP2; 2,3DMB2/4MP2 | $SiO_2$ 0.0; 0.0 | $SiO_2$ 1.75; 0.21 | $SiO_2$ 2.37; 0.54 | $SiO_2$ 0.59; 0.048 |
| 3MP2/4MP2; 2,3DMB2/4MP2 | $SiO_2$-$Al_2O_3$ 2.87; 0.69 | $SiO_2$-$Al_2O_3$ 2.44; 0.32 | $SiO_2$-$Al_2O_3$ 2.03; 0.23 | $SiO_2$-$Al_2O_3$ 2.08; 0.32 |
| 3MP2/4MP2 | $Al_2O_3$ 0.04; 0.03 | $Al_2O_3$ 2.04; 0.27 | $Al_2O_3$ 1.93; 0.24 | $Al_2O_3$ 1.75; 0.20 |

\* = calcination temperature
n.a. = not available
MP2 = trans 3-methylpent-2-ene
MP2 = cis and trans 4-methylpent-2-ene
2,3DMB2 = 2,3-dimethylbutene-2

The results summarized in Table 1 clearly show 1) the use of 12-tungstophosphoric acid instead of ammonium metatungstate increases the acidity of the silica catalyst dramatically and 2) the aluminum phosphotungstate salt on zirconia is more acidic than either 12-tungstophosphoric acid or ammonia metatungstate on zirconia.

Example 7

Preparation of 0.3% Pt on Supported Catalysts by Chloroplatinic Acid 9.97 grams of the supported 12-tungstophosphoric acid, exchanged aluminum 12-tungstophosphoric acid, tungsten oxide and tungsten oxide plus Al described in Examples 2–5 were impregnated with 2.10 cc of a chloroplatinic acid solution containing 0.15 g of Pt per 1.00 cc and further diluted with water to reach the incipient wetness volume. These impregnates were then dried at 110° C. overnight and then calcined at 300° C. in air for three hours.

Example 8

Preparation of 0.3% Pt on Supported Catalyst by Tetrammine Platinum Hydroxide 9.97 grams of the supported 12-tungstophosphoric acid, exchanged aluminum 12-tungstophosphoric acid salt, tungsten oxide, and tungsten oxide plus Al described in Examples 2–5 were impregnated by incipient wetness using 2.0 g of a Pt tetrammine hydroxide solution (1.47 wt. % Pt) diluted to the incipient wetness volume. These catalysts were then dried at 110° C. overnight and calcined at 300° C. in air for three hours.

Example 9

The catalysts were run in a fixed bed micro reactor equipped with on-line GC analysis under n-heptane isomerization conditions. The catalyst, together with a quartz powder diluent, was added to a 6 inch reactor bed. A thermocouple was inserted into the center of the bed. The catalysts were calcined at 300° C. immediately prior to use and reduced in $H_2$ at 200° C. for 1 hour. The feed was introduced via a liquid feed pump. The runs were made at 160 psi with a $H_2$/n-heptane feed ratio of 7 and a weight hourly space velocity of 11. For those runs where a temperature ramping profile was followed, the isomerization was run for 4.5 hours during which three data points were collected and averaged. The temperature then increased 10 to 20 degrees and catalyst data measured another four and a half hours. The results are shown in FIGS. 2–6.

The catalysts of the FIGS. 1–5 and Example 9 are as follows:

Catalyst A is exchanged aluminum 12-tungstophosphoric acid with platinum supported on zirconium hydroxide where the platinum was incorporated using the cationic precursor platinum tetrammine hydroxide as the precursor as in Example 3 and 8. Catalyst B is the same as catalyst A except the platinum precursor was chloroplatinic acid as in Examples 3 and 7. Catalyst C is 12-tungstophosphoric acid and platinum supported on zirconium hydroxide where the platinum precursor was platinum tetrammine hydroxide as in Examples 2 and 8. Catalyst D is the same as catalyst C except that the platinum was incorporated using chloroplatinic acid as in Examples 2 and 7. Catalyst E is tungsten oxide with aluminum and platinum on zirconium hydroxide where the platinum was incorporated using platinum tetrammine hydroxide as in Examples 5 and 8. Catalyst F is the same catalyst as Catalyst E except that the platinum was incorporated using chloroplatinic acid as in Examples 5 and 7. Catalysts G, H, I, J, K and L are catalysts on silica supports. Catalysts G and H are exchanged aluminum 12-tungstophosphoric acid and platinum where the platinum is incorporated via platinum tetrammine hydroxide and chloroplatinic acid respectively, Examples 3 and 8, and 3 and 7 respectively. Catalyst I and J are 12-tungstophosphoric acid and platinum where the platinum was incorporated via platinum tetrammine hydroxide and chloroplatinic acid respectively, Examples 2 and 8 and 2 and 7 respectively. Catalysts K and L are tungsten oxide and platinum where the platinum was incorporated via platinum tetrammine hydroxide and cholrplatinic acid, respectively, Examples 4 and 8 and 4 and 7 respectively.

Figure 2:
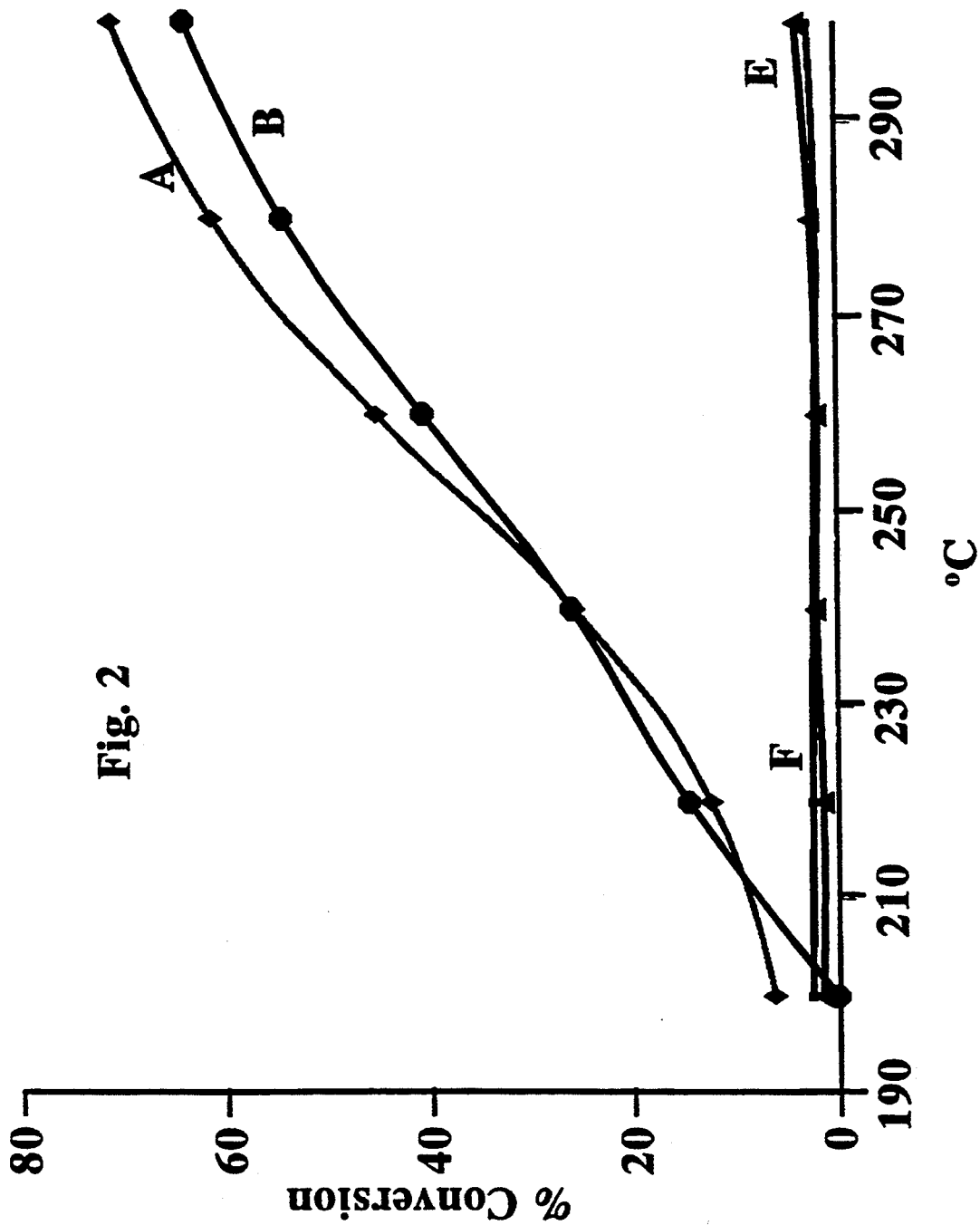
FIG. 2 again compares catalysts A and B to typical prior art catalysts E and F. Catalysts E (solid line) and F (line with boxes) are tungsten oxide supported on zirconium hydroxide containing aluminum and platinum with the platinum precursor being either platinum tetrammine hydroxide or chloroplatinic acid, respectively. Catalysts E and F containing tungsten oxide and alumina in place of the exchanged aluminum 12-tungstophosphoric acid are not active.
Figure 3:
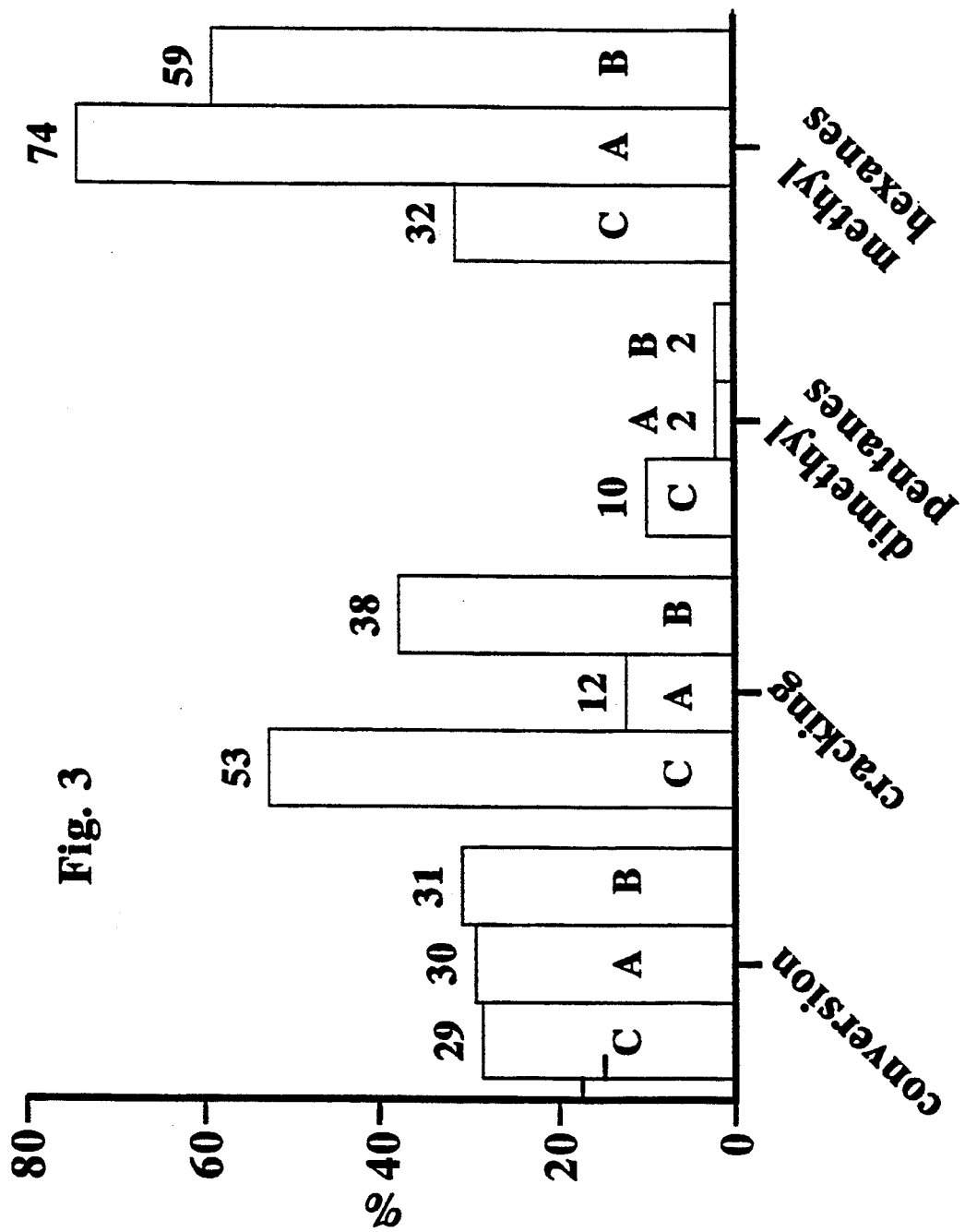
FIG. 3 shows that catalysts A and B exhibit less cracking than a typical prior art platinum containing sulfated zirconia catalyst (diagonal bar) (see U.S. Pat. No. 5,120,898) when run at comparable conversions. Similar conversions were obtained by operating catalysts A and B at 240° C. while the sulfated zirconia catalyst was run at 180° C.

FIG. 1 shows that the Al-HPW is more effective than the pure HPW acid when impregnated onto Zr(OH)$_4$. The platinum precursor has little effect on the relative activity. FIGS. 1 and 2 show that either the plain HPW precursor or the ammonium metatungstate (AMT) precursors with added (Al) do not form effective catalysts regardless of the platinum precursor. The Al-HPW precursor on zirconia however is active and shows increasing activity with rising temperature from 220° to 300° C. FIG. 3 shows the interesting selectivity behavior of Al-HPW on Zr(OH)$_4$ made with the tetrammine platinum hydroxide precursor. At comparable conversions to a ZrO$_2$/SO$_4$ catalyst as well as Al-HPW/Zr(OH)$_4$ made with chloroplatinic acid the selectivity to cracked products is dramatically diminished. This is quite important and unexpected.

FIG. 4 shows the behavior of the HPW and Al-HPW catalysts on SiO$_2$. In this case the addition of aluminum is not critical, but the platinum precursor becomes the important parameter. Only those catalysts made with chloroplatinic acid are active; platinum tetrammine hydroxide produces inferior catalyst. The comparative example catalyst made with the AMT percursor, i.e., WO$_3$/SiO$_2$ and (WO$_3$ & Al)/SiO$_2$ are also not active at all. FIG. 5 shows that the selectivity to cracking at comparable conversions is lower on the HPW on SiO$_2$ catalyst than on the Al-HPW on SiO$_2$ catalyst.

What is claimed is:

1. A solid acid catalyst composition comprising a zirconium hydroxide support about 0.01 to about 10 wt. % of a Group VIII metal and about 0.01 to about 60 wt. % of an exchanged heteropolyacid salt selected from the group consisting of the exchanged aluminum acid salt of 12-tungsto- phosphoric acid, the exchanged aluminum acid salt of 12-tungstosilicic acid, and mixtures thereof.

2. A catalyst composition according to claim 1 wherein said Group VIII metal is selected from the group consisting of iron, cobalt, nickel, ruthenium, rhodium, palladium, osmium, iridium, platinum, and mixtures thereof.

3. A catalyst composition according to claim 2 wherein said Group VIII metal is a Group VIII noble metal.

4. A catalyst composition according to claim 3 wherein said Group VIII noble metal is platinum.

5. A solid acid catalyst composition according to claim 1, said heteropoly acid is the exchanged aluminum salt of 12-tungstophosphoric acid and said Group VIII metal is platinum.

6. A process of preparing a solid acid catalyst comprising a support, about 0.01 wt. % to about 10 wt. % of a Group VIII metal, and about 0.01 to about 60 wt. % of an exchanged heteropolyacid salt comprising the steps of (a) impregnating a heteropolyacid selected from the group consisting of the exchanged aluminum acid salt of 12-tungstophosphoric acid, the exchanged aluminum acid salt of 12-tungstosilicic acid, and mixtures thereof onto a zirconium hydroxide support;

(b) impregnating Group VIII metal onto said support before, during, or subsequent to step (a);

(c) activating said impregnated zirconium hydroxide support prior to and following said impregnation step (b) if said Group VIII metal is impregnated subsequent to step (a) or activating said impregnated support after said impregnation of a heteropolyacid salt if said Group VIII metal is impregnated before or during step (a) to form a catalyst.

7. A process of preparing a solid acid catalyst according to claim 6 wherein said Group VIII metal is impregnated via a solution selected from the group consisting of chloroplatinic acid, ammonium tetrachloroplatinate (II), ammonium hexachloroplatinate (IV), chloroiridic acid, tetrammine platinum hydroxide, tetrammine platinum chloride, and dinitrodiammineplatinum (II).

* * * * *